United States Patent [19]

Schweizer

[11] Patent Number: 4,992,617
[45] Date of Patent: Feb. 12, 1991

[54] ISOMERIZATION USING NOBLE METAL ACIDIC ZEOLITES

[75] Inventor: Albert E. Schweizer, Baton Rouge, La.

[73] Assignee: Exxon Research and Engineering Company, Florham Park, N.J.

[21] Appl. No.: 292,690

[22] Filed: Jan. 3, 1989

[51] Int. Cl.$^5$ .............................................. C07C 5/13
[52] U.S. Cl. ..................................... 585/739; 585/751
[58] Field of Search ............................... 585/739, 751

[56] References Cited

U.S. PATENT DOCUMENTS 3,190,939  6/1965  Benesi ................................. 585/739
4,118,430 10/1978  Mooi .................................. 585/950
4,431,574  2/1984  Bournonville et al. ............. 585/273
4,855,530  8/1989  LaPierre et al. ..................... 585/739

Primary Examiner—Curtis R. Davis
Attorney, Agent, or Firm—Henry E. Naylor

[57] ABSTRACT

Disclosed is a method for isomerizing paraffinic hydrocarbons which comprises contacting the paraffinic hydrocarbon with a noble-metal containing zeolite catalyst under isomerization conditions. The noble-metal catalyst are prepared by treating a zeolite selected from the acidic zeolites, LZ-210 type zeolites, and mordenite, with a noble-metal compound selected from Pt(acetylacetonate)$_2$ and Pd(acetylacetonate)$_2$.

4 Claims, 1 Drawing Sheet

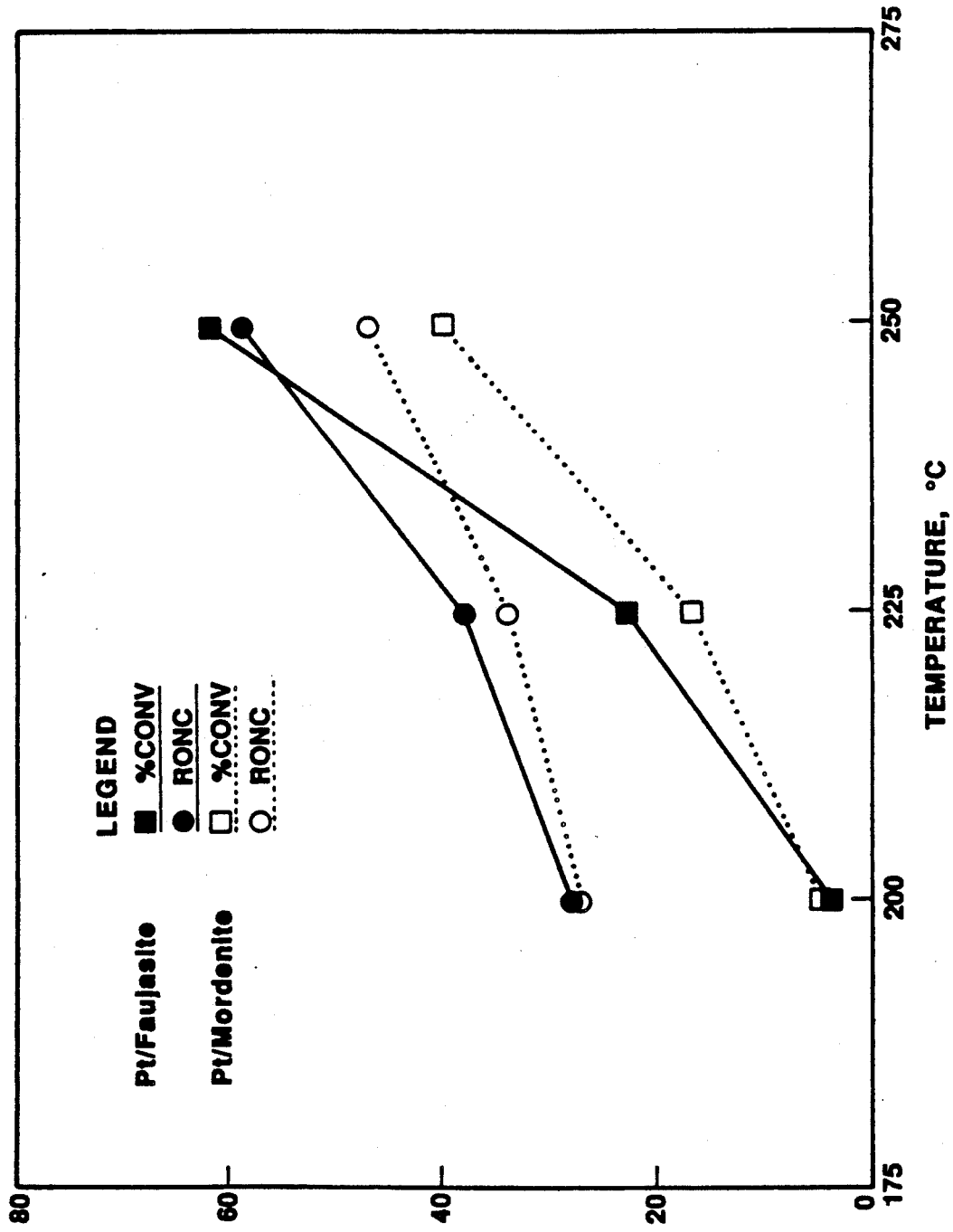
FIGURE

ISOMERIZATION USING NOBLE METAL ACIDIC ZEOLITES

FIELD OF THE INVENTION

The present invention relates to a process for isomerizing hydrocarbons by use of noble-metal containing zeolites.

BACKGROUND OF THE INVENTION

Catalytic isomerization is an important refinery process for converting normal paraffins to their higher octane isomer counterparts. Catalysts employed to catalyze isomerization reactions include Friedal-Crafts catalysts, such as aluminum chloride; noble-metal catalysts, such as platinum on halogenated alumina; and more recently, crystalline aluminosilicate zeolites. Both natural and synthetic crystalline aluminosilicates have been employed. These include zeolite X, Y, as well as synthetic mordenite, especially hydrogen form mordenite.

While various degrees of commercial success have been achieved using such catalyst systems, there is still a need in the art for catalysts having improved isomerization properties.

SUMMARY OF THE INVENTION

In accordance with the present invention, there is provided a process for isomerizing paraffinic hydrocarbons by reacting solid hydrocarbons, at isomerization conditions with a noble-metal-containing zeolite selected from acidic faujasites, LZ-210 type zeolites, and mordenite, which noble-metal containing zeolite is prepared by:

(a) treating a zeolite with Pt(acetylacetonate)$_2$ or Pd(acetylacetonate)$_2$, or both, for an effective amount of time to form a substantially homogeneous mixture and to incorporate the platinum and/or palladium into the near regions of the zeolite, but not disperse it throughout the entire zeolite; and (b) calcining the so treated zeolite at a temperature from about 250° C. to about 600° C. for an effective amount of time.

In preferred embodiments of the present invention, the zeolite is an acidic faujasite and is treated with the noble metal containing compound as a dry-mix.

In other preferred embodiments of the present invention, the isomerization conditions include a temperature from about 400° C. to 500° C., a pressure of about 0 to 1000 psig, and a hydrogen treat rate of about 1000–5000 SCFB.

BRIEF DESCRIPTION OF THE FIGURE

The sole FIGURE thereof is a graphical representation depicting activity and selectivity advantages for hexane isomerization of the catalysts of this invention over conventionally produced noble-metal zeolite catalysts.

DETAILED DESCRIPTION OF THE INVENTION

Zeolite compositions suitable for use herein are the acidic, or hydrogen form, 12-ring zeolites; such as acidic faujasite, LZ-210 type zeolite, and mordenite. Preferred are acidic faujasite and mordenite, and most preferred is acidic faujasite.

Mordenites expressed in terms of mole ratios of oxide, may be represented as follows:

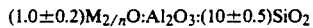

$$(1.0 \pm 0.2)M_{2/n}O:Al_2O_3:(10 \pm 0.5)SiO_2$$

wherein M is an alkali or alkaline-earth metal, preferably sodium or potassium; and n is the valence of M.

Because the alkali and alkaline-earth metal form of zeolite is not particularly effective for the isomerization hydrocarbons, some or all of said metal is replaced with hydrogen ions, thereby resulting in a more advantageous hydrogen form for isomerization. This substitution of hydrogen for alkali and alkaline-earth metal can be accomplished by any conventional means. Non-limiting examples of such means include the direct replacement of the metal ions with hydrogen ions by ion exchange metals using an acidified aqueous solution. Another method involves the substitution of metal ions with ammonium ions followed by decomposition of the ammonium form using a high temperature oxidative treatment. Combinations of the acid and ammonium treatment for mordenite are disclosed in U.S. Pat. No. 3,475,345 and U.S. Pat. No. 3,442,794, both of which are incorporated herein by reference. In U.S. Pat. No. 3,475,345, a sodium form synthetic mordenite is converted to a hydrogen form in a three-step pretreatment procedure. That is, powered mordenite is first subjected to a hot acid treatment, followed by a cold acid treatment, followed by treatment with an ammonium compound.

It is preferred to use a mordenite having a relatively high silica to alumina ratio. Typically, a silica to alumina ratio of about 10:1 is observed for a sodium form synthetic mordenite and is substantially unchanged if an ammonium treatment is used to convert the mordenite to the hydrogen form. If the mordenite powder is subjected to an acid treatment as taught in U.S. Pat. No. 3,597,155, an increase in the silica to alumina ratio is effected. The acid treatment is believed to cause a reduction of the framework tetrahedra aluminum atoms, thus increasing the proportion of silica atoms present in the zeolitic structure, as taught in U.S. Pat. No. 3,507,931, a silica to alumina ratio above about 20:1 significantly improves the isomerization of light hydrocarbons. U.S. Pat. No. 4,018,711 also teaches that isomerization performance is improved if a pretreated mordenite powder having a silica to alumina ratio of at least 19:1 is incorporated in a catalyst composition. Further, the relatively high surface area, high silica to alumina mordenites taught in U.S. Pat. No. 4,735,929 are also suitable for use herein.

Acidic faujasites are generally produced by substituting hydrogen ions for alkaline ions in an alkaline Y faujasite. The chemical formula alkaline Y faujasite, expressed in terms of mole ratio of oxides may be written as:

$$(0.714\ 1.1)M_{2/n}O:Al_2O_3:xSiO_2:yH_2O$$

wherein M is an alkali or alkaline-earth metal, n is the valence of M, x is a value greater than 3 and up to about 6, and y may be a value up to about 9. Zeolite Y has a characteristic X-ray powder diffraction pattern which may be employed with the formula for identification. Zeolite Y is described in more detail in U.S. Pat. No. 3,130,007, which is also incorporated herein by reference. The hydrogen, or acid form of the faujasite is obtained by means similar to that for mordenite, discussed above, except acidic faujasite is usually not obtained by direct replacement of the metal ions with hydrogen ions using an acidified aqueous solution.

The chemical formula for LZ-210 zeolite, expressed in terms of mole ratio of oxides, may be written as:

$$(0.7-1.1)M_{2/n}O:Al_2O_3:(6-20)SiO_2:yH_2O$$

wherein M is an alkali metal or alkaline-earth metal, n is the valence of M, and y may have a value up to about 8 depending on the identity of M and the degree of hydration of the crystalline zeolite. Zeolite LZ-210, its X-ray diffraction pattern, its properties, and method of preparation are described in U.S. Pat. No. 4,503,023, which is incorporated herein by reference. By LZ-210 type zeolite, I mean LZ-210 zeolite itself or a zeolite which is isostructural to LZ-210.

Another preferred catalyst of this invention, ultrastable zeolite Y, (USY), is described in detail in U.S. Pat. No. 3,449,070 which is also incorporated herein by reference. USY-zeolite, which is ultrastable at elevated temperatures, can be written as:

$$xM_{2/n}O.Al_2O_3:(3.5-7)SiO_2:yH_2O$$

where M represents $H^+$ or any other cation except the alkalis; n is the valence of M and can be 0 to 1; y can vary from 0 to 9; and x is from 0 to 1.

The compositions of the present invention are prepared by treating the zeolite with an effective amount of a noble-metal containing compound selected from Pt(acetylacetonate)$_2$ or Pd(acetylacetonate)$_2$, also sometimes referred to herein as Pt(acac)$_2$ and Pd(acac)$_2$. An effective amount of noble metal compound is that amount which will result in a catalyst containing from about 0.5 to 10 wt. %, preferably from about 0.5 to 5 wt. %, and more preferably from about 0.75 to 1.5 wt. % noble metal, based on the total weight of the catalyst. The zeolite can be treated by merely mixing together the Pt- and/or Pd(acac)$_2$ and zeolite; or by treating the zeolite with the Pt- and/or Pd(acac)$_2$ in an organic solvent, such as toluene, for an effective amount of time. Effective amount of time means for a time which will allow the Pt and/or Pd to be introduced into the zeolite at or near the surface, but not so long as to allow the Pt and/or Pd to be impregnated throughout the entire zeolite structure. That is, the noble metal will be impregnated no more than 90%, preferably no more than 80%, into the interior of the zeolite. After the zeolite is treated with the Pt- and/or Pd(acac)$_2$, it is calcined at a temperature from about 250° C. to about 600° C. If the zeolite and the Pt or Pd(acac)$_2$ are dry-mixed, the drymix must be calcined for the same effective amount of time as indicated above. For example, at a temperature from about 300° C. to about 400° C. an effective amount of time will be from about 5 minutes to about 4 hours.

It has unexpectedly been found that only when the noble metal containing zeolite materials of the present invention are prepared by the method of this invention, do they show unexpected activity for isomerization. That is, the catalyst maintains an unexpectedly high degree of activity for an extended period of time. If platinum, and/or palladium, is incorporated into the zeolite in accordance with prior art methods, such as by ion-exchange, or by treatment with an aqueous solution of a salt of a platinum or palladium complex, such as hexachloroplatinic acid, dinitrodiaminoplatinum or platinum tetramine chloride, the resulting Pt and/or Pd-containing zeolite do not show the unexpected advantages for isomerization.

Hydrocarbons which may be isomerized by the process of this invention include paraffinic and olefinic hydrocarbons typically having 4–20, preferably 4–12, more preferably about 4–6 atoms; aromatic hydrocarbons such as xylenes. The preferred chargestock is comprised of paraffinic hydrocarbons typified by butanes, pentanes, hexanes, heptanes, etc.

The instant catalysts may find use in isomerization processes wherein the position of the double bond is changed as typified by the conversion of butene-1 to butene-2. They may also be used in disproportionation processes such as the conversion of toluene to benzene and xylene or in transalkylation processes such as the reaction of benzene and zylene to produce toluene.

Prior to use of the calcined catalyst composition, it is preferred to precondition the composition by heating, in a flowing stream of hydrogen, to 450° F.–1000° F., preferably 500° F.–675° F. say 550° F. for 2–10 hours, preferably 2–4 hours, say 3 hours. Pretreating, like isomerization, is preferably carried out under substantially anhydrous conditions.

Isomerization in accordance with the process of this invention may be carried out by passing the charge isomerization hydrocarbon into contact with the preconditioned catalyst in the presence of hydrogen, at the following conditions:

| Conditions | Broad | Preferred | Typical |
|---|---|---|---|
| Temperature, °F. | 400–500 | 400–450 | 435 |
| Pressure, psig | 0–1000 | 0–300 | 250 |
| LHSV | 0.1–20 | 0.1–2 | 1 |
| Hydrogen Rate, SCFB | 1000–5000 | 1500–2500 | 2300 |

The catalyst may be in the form of granules, e.g., 10 to 25 mesh Tyler Standard screen Scale, and preferably is in the form of pellets or extrusions having a diameter of about 1/16 inch. The reaction is suitably carried out over a fixed bed of catalyst with the hydrogen and feedstock passing downwardly through the catalyst bed. Unreacted hydrogen may be separated from the effluent stream from the catalyst bed and recycled to the process.

Operating temperature and catalyst activity are correlated with space velocity to give reasonably rapid processing of the feedstock at catalyst deactivation rates which insure maximum on-stream time of the catalyst between periods of regeneration.

As the catalyst ages, its activity for the desired reaction tends to slowly diminish. The catalyst may be maintained at or periodically brought back to approximately its initial level of activity by increasing the operating temperature as the catalyst ages.

The following examples serve to more fully describe the present invention. It is understood that these examples are not intended to limit the true scope of this invention, but rather are presented for illustrated purposes.

N-HEXANE TEST

To illustrate the hydroisomerization activity and selectivity of the catalysts of this invention n-hexane was isomerized at a standard set of conditions of temperature, hydrogen pressure and rate, and at a fixed space velocity (weight liquid feed per hour per weight of catalyst). The conversion is measured by the disappearance of the n-hexane feed, and the selectivity by the increase in research octane number, clear (RONC). This value is calculated from the known octane number of the hexane isomers. The feed, n-hexane, has a RONC of 25, while the isomers are all much higher, 73 to 104.

COMPARATIVE EXAMPLE 1

A platinum on hydrogen-mordenite was prepared by ion-exchanging a hydrogen-mordenite with $Pt(NH_3)_4^{2+}$, washing and air calcining. The mordenite has a molar ratio of $SiO_2$ to $Al_2O_3$ of 16.3, less than 0.01% sodium, and after exchange contained 0.5% Pt.

EXAMPLE 1

A platinum on LZY-82 was prepared by blending together 100 gms of calcined LZY-82 (an acidic faujasite available from Union Carbide Co.) with 1.32 gms of $Pt(acetylacetonate)_2$ then rapidly calcining the mixture. This resulted in a Pt on acidic faujasite containing 0.66 wt. % Pt.

The above two catalysts were tested in a ½ inch diameter stainless steel reactor mounted in an electrically heated sand bath. The temperature was varied between 200° C. and 250° C. At these temperatures, the hydrocracking of the hexane to lower carbon number products is small (approximately 2 wt. % of the total feed). Further, the catalysts show very little decline in activity over hours of operation at these conditions, indicating no significant coking has occurred.

The precise conditions of the above catalyst testing was a total pressure of 250 psig, 3000 SCF of hydrogen per barrel of hexane feed, and one space velocity. At these conditions, in the temperature range of 200° C. to 250° C., the thermodynamic n-hexane conversion ranges from 90 to 80%, so that catalysts more active than the Pt on mordenite by conventional means are expected to be found. The conversion and octane results for both the comparative catalyst and the catalyst of this invention can be found in the figure hereto.

What is claimed is:

1. A method for isomerizing paraffinic hydrocarbons, which method comprises contacting a paraffinic hydrocarbon, under isomerization conditions, with a noble metal containing zeolite prepared by: (a) dry-mixing a 12-ring acidic zeolite, other than mordenite, with a noble-metal compound selected from $Pt(acetylacetonate)_2$ and $Pd(acetylacetonate)_2$ for an effective amount of time to incorporate Pt and/or Pd into the pore surface regions of the zeolite, but not to disperse the Pt and/or Pd throughout the entire zeolite; and (b) calcining the so treated zeolite at a temperature from about 250° C. to about 600° C.

2. The method of claim 1 wherein zeolite is an acidic faujasite.

3. The method of claim 2 wherein the acidic faujasite is an ultrastable Y faujasite.

4. The method of claim 1 wherein the dry-mix is calcined at a temperature from about 300° C. to about 400° C.

* * * * *